(12) United States Patent
Hiselius et al.

(10) Patent No.: US 6,427,800 B1
(45) Date of Patent: Aug. 6, 2002

(54) EAR PLUG AND METHOD OF MANUFACTURING AN EAR PLUG

(75) Inventors: Per Hiselius, Lund; Lars Nilsson, Ängelholm, both of (SE)

(73) Assignee: Dalloz Safety AB, Billesholm (SE)

( * ) Notice: Subject to any disclaimer, the term of this patent is extended or adjusted under 35 U.S.C. 154(b) by 0 days.

(21) Appl. No.: 09/704,607

(22) Filed: Nov. 3, 2000

(30) Foreign Application Priority Data

Nov. 3, 1999 (SE) ................................................. 9903999

(51) Int. Cl.⁷ ................................................. A61B 7/02
(52) U.S. Cl. ........................ 181/135; 128/864; 128/865
(58) Field of Search .................. 181/135, 129; 128/864, 165

(56) References Cited

U.S. PATENT DOCUMENTS

| | | | |
|---|---|---|---|
| 2,785,675 A | 3/1957 | Berkman | |
| 3,771,521 A | 11/1973 | Kittredge | |
| 4,160,449 A | 7/1979 | Wade | |
| 4,540,063 A | 9/1985 | Ochi et al. | |
| 4,552,137 A | 11/1985 | Strauss | |
| 5,573,015 A | * 11/1996 | Williams | 128/864 |
| 5,904,143 A | 5/1999 | Magidson et al. | |

FOREIGN PATENT DOCUMENTS

| | | |
|---|---|---|
| CA | 1 168 589 | 6/1984 |
| EP | 0 050 601 | 4/1982 |
| EP | 0 847 736 | 6/1998 |
| SE | 341 784 | 1/1972 |
| SE | 406 152 | 1/1979 |
| SE | 81029316 | 5/1981 |
| SE | 442 946 | 2/1986 |

OTHER PUBLICATIONS

Copy of International Search Report dated Sep. 8, 2000.

* cited by examiner

*Primary Examiner*—Khanh Dang
(74) *Attorney, Agent, or Firm*—Burns, Doane, Swecker & Mathis LLP

(57) ABSTRACT

The invention relates to a sound-attenuating ear plug, comprising an elongate elastic body (103) adapted to be inserted at least partially into an auditory meatus. A foil (117) which is rounded in the longitudinal direction (115) of the body (103) and which is extended transversely of this longitudinal direction (115) is responsible for the major part of the sound-attenuating effect of the ear plug. The invention also relates to a method of manufacturing such an ear plug.

33 Claims, 3 Drawing Sheets

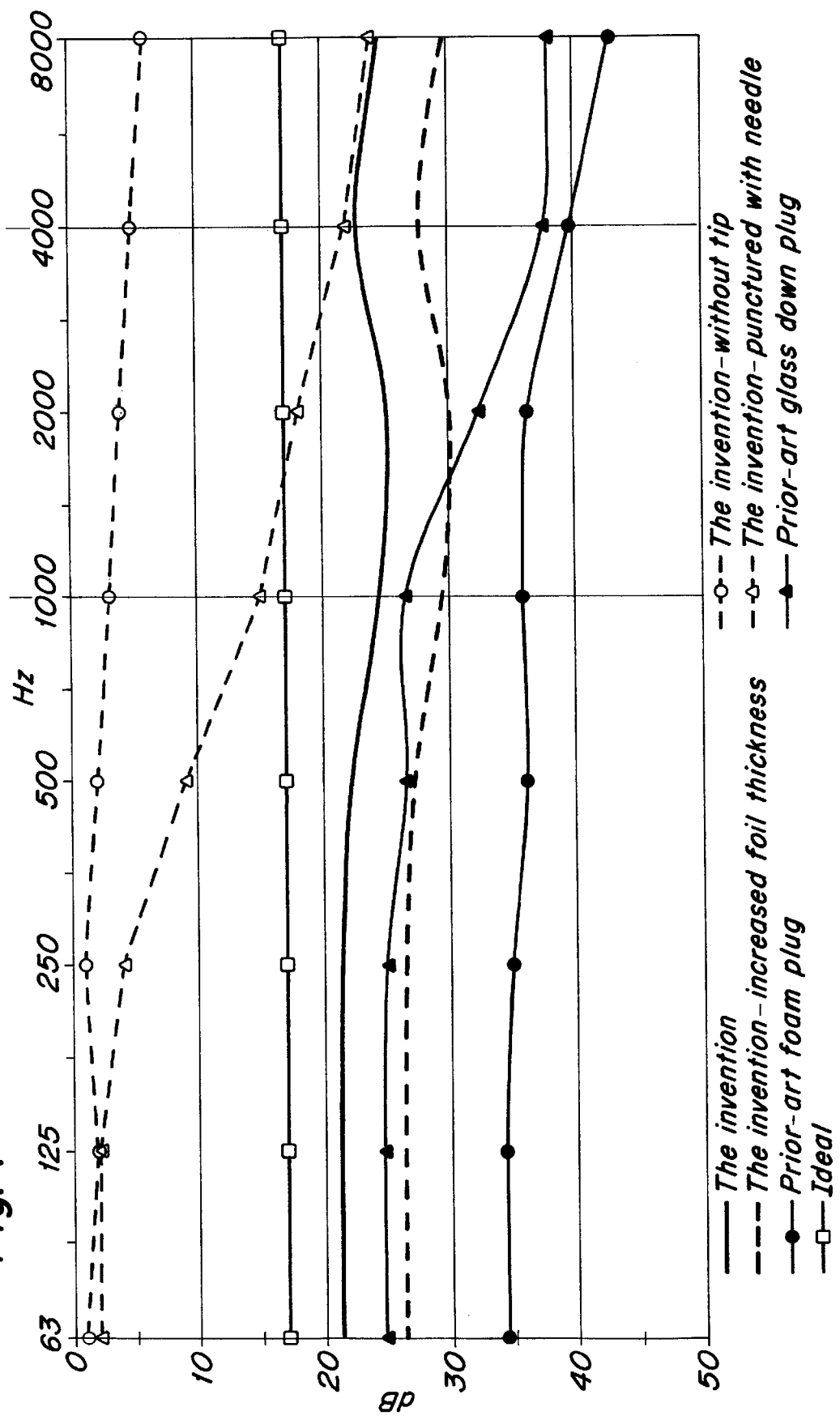

EAR PLUG AND METHOD OF MANUFACTURING AN EAR PLUG

TECHNICAL FIELD

The present invention relates to the technical field of sound-attenuating ear plugs and in particular to the kind which comprises an elongate body of elastic material, which is adapted to be inserted into the auditory meatus or canal of a user's ear. The invention also relates to a method of manufacturing an ear plug. The invention is particularly directed to indicating an ear plug having an improved attenuation characteristic.

Here the term "plug" refers to an ear protector which, when used, is at least partially inserted into an auditory meatus of a user's ear, in contrast to earmuffs which are to be applied to the outside of the user's ear.

BACKGROUND OF THE INVENTION

In the technical field of ear plugs, it is known that it is desirable but difficult to obtain an attenuation curve which is substantially frequency-independent or which at least does not vary excessively with varying frequency. FIG. 1 of the accompanying drawings shows, by means of a curve marked "Ideal", an example of such an ideal attenuation characteristic which in this example is at a constant attenuation value of 17 dB up to 8 kHz. However, prior-art ear plugs exhibit attenuation characteristics which are rather far from such an ideal-straight characteristic. A particular problem is that the attenuation is often undesirably high within the frequency range that is most important to the perception of speech, i.e. substantially in the range of 1 kHz to 4 kHz (marked with vertical lines in FIG. 1). This problem is discussed, for instance, in SE 8102931-6 (Racal), in which the aim is a substantially straight attenuation characteristic up to 2 kHz. A generally known problem is that it is difficult to provide suitable low-frequency attenuation while not excessively attenuating high-frequency sound.

The Applicant of the present application currently manufactures and sells glass "down" ear plugs of the kind which is described in EP 0 050 601 and which is schematically shown in FIG. 2 of the accompanying drawings. The ear plug consists of an elongate body 3 which is made of elastic material and which is surrounded by a sheath 1 of flexible plastic material. Referring to its direction of insertion into the auditory meatus, the plug has a front end A and a rear end B.

The sheath 1 serves to facilitate the handling of the plug and to provide improved hygiene. The sheath 1 also helps to maintain the desired shape of the elastic body 3. At the rear end B of the plug, the sheath 1 has a circumferential more rigid portion 7, such as an outwardly directed collar or flange portion. The sheath 1 is made of a deep-drawn, thin and flexible film made of, for instance, polyvinyl chloride (PVC), polyurethane (PUR) or polyethylene (PE). Since the sheath is thin and flexible, a satisfactory adjustment is obtained between the elastic body and the inner wall of the auditory meatus.

The elastic body of the ear plug which is currently manufactured is made of glass down and is considerably blocking as regards air-flow, i.e. very airtight and thus provides a relatively high sound-attenuating effect. The curve which is marked "Prior-art glass down plug" in the diagram in FIG. 1 shows the result of a measurement of the attenuation (according to ISO 4869-1) of this prior-art glass down plug at the frequencies which are specifically indicated on the x-axis in the diagram. It is to be noted that the attenuation characteristic of the plug deviates considerably from the ideal, straight characteristic, in particular in the range of speech where the attenuation is considerably higher.

The Applicant of the present application presently manufactures and sells also elastic ear plugs made of foam material. The curve marked "Prior-art foam plug" in the diagram in FIG. 1 shows the result of a measurement of the attenuation of this prior-art foam plug. Admittedly, the characteristic is somewhat straighter than in the case of the glass down plug of FIG. 2, but the attenuation of the foam plug is not lower in the range of speech but on the contrary higher, and therefore the perception of speech as such is not improved. For higher frequencies, the attenuation amounts to about 40 dB.

SUMMARY OF THE INVENTION

It is an object of the invention to provide a sound-attenuating ear plug having improved attenuation characteristic. A particular object of the invention is to indicate an ear plug which reduces the above-identified problems concerning (i) nonlinear or frequency-dependent attenuation and (ii) excessive attenuation in the range of speech.

These objects are achieved by means of an ear plug having the features defined in the appended claims.

According to one aspect of the invention, a sound-attenuating ear plug is provided, comprising an elongate elastic body adapted to be inserted at least partially into an auditory meatus, said body being essentially non-attenuating as regards sound, and a foil held by said body, as seen along a longitudinal axis of said body, in a three-dimensionally rounded concave or convex shape which provides such acoustical properties that the foil is responsible for the major part of the sound-attenuating effect of the ear plug.

According to another aspect of the invention, a sound-attenuating ear plug is provided, comprising an elastic body adapted to be inserted into an auditory meatus, said elastic body being made of a material which is substantially non-attenuating as regards sound, and a sheath which at least partially surrounds the elastic body, at least a part of said sheath having acoustical properties being responsible for the major part of the sound-attenuating effect of the ear plug.

According to a further aspect of the invention, a method is stated of manufacturing an ear plug, which comprises an elongate body made of elastic material and surrounded by a sheath made of flexible plastic material, a thermoplastic plastic film or foil being deep-drawn into a sheath in a manner known per se and the sheath, subsequently or simultaneously, being filled with elastic material. According to this method, as said elastic material, use is mainly made of a material which is substantially non-blocking as regards air-flow.

According to yet another aspect of the invention, use, in an ear plug, of an airtight foil is provided, which foil is three-dimensionally rounded in the direction of the auditory meatus and is the component of the ear plug that is responsible for the major part of the sound-attenuating effect of the ear plug.

According to an additional aspect of the invention, a method is provided of controlling the sound-attenuating effect of a sound-attenuating ear plug, comprising the steps of providing the ear plug with a foil which is three-dimensionally rounded in the longitudinal direction of the auditory meatus, and choosing the thickness of the rounded foil so as to obtain a desired sound-attenuating effect of the ear plug.

The invention is based on the understanding that it is possible to obtain an improved attenuation characteristic by lowering the air-flow blocking properties of an elastic body included in the plug, and instead using a rounded foil to provide the major part of the attenuation effect of the ear plug. This is apparently a solution which goes against traditional practice within the field, where elastic materials having relatively good air-flow blocking properties are normally desired to provide the sound-attenuating effect of the plug. It has thus been found that if, for instance, the starting-point is the prior-art glass down plug which is described above with reference to FIG. 2 and which consists, on the one hand, of a thin plastic sheath and, on the other, of a glass down body having a high flow resistance, and this glass down body is replaced by an elastic body which is substantially non-blocking as regards air-flow, a sound-attenuating ear plug is provided having considerably improved frequency characteristic. The attenuation characteristic of an ear plug according to the invention can be made much flatter (more frequency-independent) compared with the attenuation characteristic of prior-art plugs, and in spite of this the attenuation can be kept on a suitable level. The background of this remarkable effect will be explained in greater detail below.

The invention is also based on the understanding that the attenuation characteristic can be improved if the foil is made to be rounded or dome-shaped in the direction of the auditory meatus. The rounded shape of the foil increases its acoustic stiffness. In particular, the acoustic stiffness can thus be increased without increasing the weight. Therefore, also a very thin and light foil can be used to provide the major part of the sound-attenuating effect of the ear plug. This property of the rounded foil can be compared to the increased strength of a Roman arch due to its arched shape. The positive effects of this acoustic stiffness on the attenuation characteristic will be explained in more detail below. In a preferred embodiment, the foil is rounded towards the eardrum, but the foil can also be rounded in the other direction, i.e. concave towards the eardrum.

During use, when the ear plug is placed in the auditory meatus, there should be substantially no transport of air between the outer ear and the inner space defined by the ear drum, the auditory meatus and the plug. Thus, the foil either independently provides the air-blocking function of the plug, or contributes to said function by e.g. being a portion of a sheath surrounding the elongate elastic body which is essentially non-blocking as regards air. The foil, which is suitably substantially airtight, extends transversely of a longitudinal axis of said body, and preferably across the central longitudinal axis of-said body.

In an advantageous embodiment of the invention a dome-shaped foil is applied on the front tip portion of the elongate elastic body. The foil is suitably, at least partially, freely movable in relation to the underlying body which provides the general shape of the dome-shaped foil.

Acoustic stiffness and acoustic resistance are two forms of acoustic impedance, which will be discussed in the following. As has been previously described, the elongate elastic body is substantially non-blocking as regards air-flow, i.e. the elastic body has a high flow resistance. The flow resistance of the elastic material which expands and distends the foil is suitably described by means of acoustic resistance $R_a$. In the relevant frequency range, this acoustic resistance $R_a$ is not to be larger than the acoustic stiffness of the rounded foil.

The acoustic stiffness of the foil is frequency dependent and can be best described by an analogue to electrical capacitance. The acoustical analogue to electrical capacitance is acoustic compliance $C_a$, which is a frequency independent constant. The acoustic stiffness $K_a$ is given by:

$$K_a = \frac{1}{j2\pi f C_a}$$

Thus, a large acoustic stiffness means a small acoustic compliance $C_a$. To obtain a sufficient sound-attenuating effect for the rounded-foil, it should have an acoustic compliance $C_a$ which is less than or equal to $1.7*10^{-11}$ m$^5$/N.

As explained above, in order for the rounded foil to provide for the major part of the sound-attenuating effect, the acoustic resistance $R_a$ of the material of the elastic body is not to be larger than the acoustic stiffness $K_a$ of the rounded foil. A suitable acoustic resistance $R_a$ in the relevant attenuation range of the ear plug-according to the invention has been found to be less than or equal to $1.2*10^9$ sN/m$^5$.

A particular advantage of the invention is that the thickness of the rounded foil can be used as a manufacturing parameter to control the sound-attenuating effect of the ear plug. In particular, the attenuation characteristic can be substantially parallel-displaced if the thickness of the foil is altered.

Preferred embodiments of the invention are defined in the dependent claims.

A preferred embodiment of an ear plug according to the invention can be manufactured according to the specifications concerning shape, foil material, deep-drawing technique, etc. which are described in above-mentioned EP 0 050 601. The sheath may thus be deep-drawn from a thermoplastic plastic film or foil made of, for instance, PVC, PUR or PE. The plastic material should have high values of breaking stress and elongation at break and a relatively low value of yield stress. If a deep-drawing technique is used in the manufacture, the plastic material should also have a small degree of shrinkage after the deep-drawing. If the ear plug according to the invention has a surrounding sheath, this can be produced with varying thickness distribution, such as described in this document.

Thus, it should be understood from the foregoing that the main function of the elastic body of an ear plug according to the invention, is to stretch or distend the foil and, in a preferred embodiment, to shape it around the tip of the body into a dome-shaped, three-dimensionally rounded foil which "points" in the direction of a longitudinal axis of the body.

Further scope of applicability of the present invention will become apparent from the detailed description given hereinafter. However, it should be understood that the detailed description and specific example, while indicating a preferred embodiment of the invention, is given by way of illustration only, since various changes and modifications within the spirit and scope of the invention will become apparent to those skilled in the art from this detailed description.

Below, a preferred embodiment of an ear plug according to the invention will be described as well as the physical principles on which the invention is based.

BRIEF DESCRIPTION OF THE DRAWINGS

The present invention will become more fully understood from the detailed description given hereinbelow and the accompanying drawings which are given by way of illustration only, and thus are not limitative of the present invention and wherein:

FIG. 1 is a diagram which shows attenuation characteristics of two prior-art ear plugs, two ear plugs according to the invention and two modified ear plugs according to the invention;

DESCRIPTION OF PREFERRED EMBODIMENTS

Figure 2:
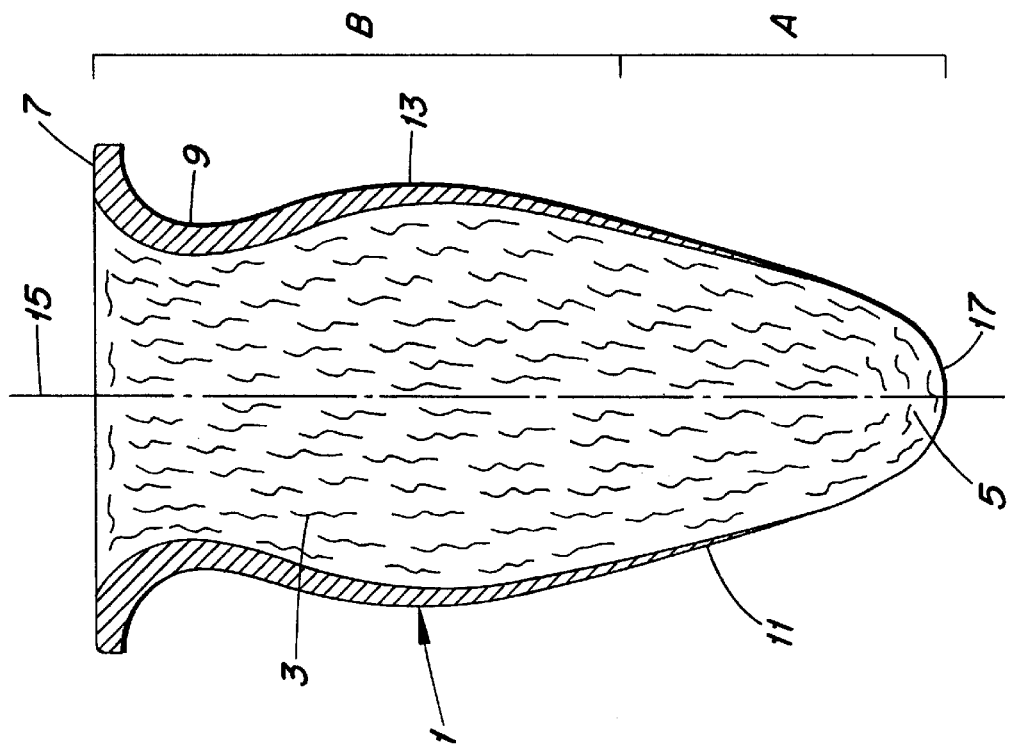
FIG. 2 shows on a larger scale a schematic longitudinal section of a prior-art glass down plug.

A preferred embodiment of an ear plug according to the invention will now be described in more detail with reference to FIG. 6. This preferred embodiment of the invention is substantially identical to the prior-art glass down plug of FIG. 2, with the exception of the selection of material in the elastic body. The same parts have generally been given the same reference numerals, the numeral 100 being added to the components of FIG. 6.

A preferred embodiment of the invention consists of (i) a deep-drawn sheath 101, which is made of a thin film of, for instance, PE plastics and which has the form of an axially elongate container, and (ii) an elastic body 103 which is surrounded by the sheath and made of fibrous material. The elastic body 103 is substantially non-blocking as regards air-flow (the acoustic resistance being no higher than $1.2*10^9$ sN/m$^5$) and, in the preferred embodiment, it is made of polymer fibre material, such as polyester, polypropylene, polyether, polyamide, etc. The fibres can be bonded (chemically, mechanically or in some other way) or non-bonded.

Along its longitudinal direction or longitudinal axis 115, the plug has a front portion A and a rear portion B. The front portion A is substantially conically tapered and ends in a bluntly three-dimensionally rounded or dome-shaped tip 105. The rear portion B of the plug is curved outwards and has a rear flange 107 and a neck portion 109.

In the same manner as in the prior-art glass down plug, the sheath 101 may have various thickness in the portions 111, 113 and 117 corresponding to the portions A, B and the tip 105 of the plug, respectively. The sheath 101 may, for instance, have a thickness in the range of 0.005 mm to 0.2 mm. Foils thinner than 0.005 mm are probably too difficult to produce, and a thickness of more than 0.2 mm probably results in too high an attenuation. In the embodiment in question which was analysed when preparing the attenuation curve marked "the invention" in FIG. 1, the foil thickness was about 0.04 mm in portion B and 0.02 mm in portion A. The rounded tip 117 of the sheath 101 which corresponds to the tip 105 of the plug, i.e. the foil portion which above is called "rounded foil" was measured to be 0.03 mm. The acoustic compliance of the foil is not higher than $1.7*10^{-11}$ m$^5$/N.

Figure 6:
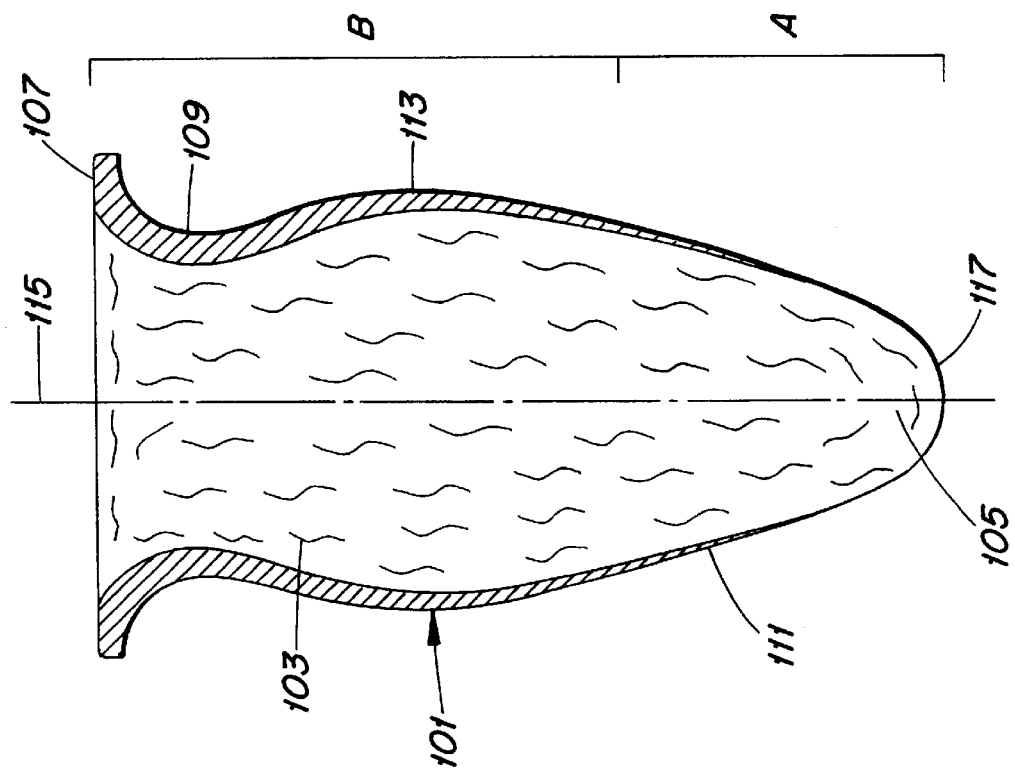
FIG. 6 shows on a larger scale a schematic longitudinal section of an embodiment of an ear plug according to the invention.
Figure 3:
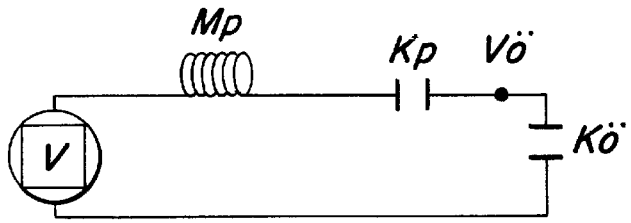
FIG. 3 shows an electric circuit analogy for a prior-art foam plug.
Figure 4:
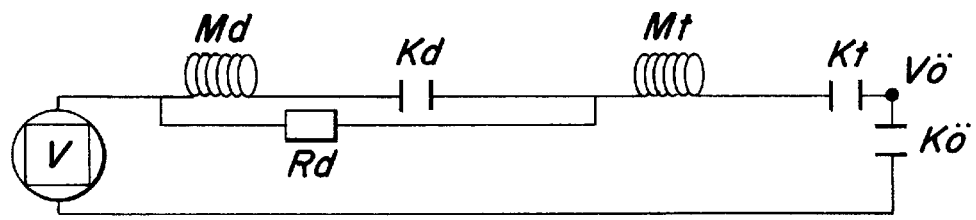
FIG. 4 shows an electric circuit analogy for a prior-art glass down plug.

With the aim of explaining the remarkable effect of the invention, reference is now being made to FIGS. 3–5 which show electric circuit analogies for, respectively, two prior-art ear plugs and an inventive ear plug of the kind which is shown in FIG. 6.

An ear plug can generally be characterised by its acoustic mass Mp and its acoustic stiffness Kp. The acoustic mass Mp is closely related to the physical mass of the plug which is set in motion by the external sound pressure. Kö indicates the acoustic stiffness of an air volume enclosed in the auditory meatus. V indicates the external sound pressure, whereas the experienced sound pressure is marked Vö in the circuit analogies. In such a transition between an acoustic and an electric diagram, a high acoustic stiffness will correspond to a low capacitance.

First reference is made to FIG. 3, which shows an electric circuit analogy for the prior-art foam plug which is currently manufactured and offered for sale by the Applicant. Given the above-mentioned designations, this prior-art foam plug essentially has a resonance frequency Fr which is dependent on Kp, Kö and Mp according to the relation (1) below:

$$Fr \sim \sqrt{\frac{Kp + Kö}{Mp}} \quad (1)$$

As indicated above, many prior-art ear plugs exhibit an excessive attenuation at high frequencies, which is particularly undesirable within-the range of speech. Generally, the attenuating effect increases considerably above the resonance frequency Fr. In principle, the undesired increased attenuation in the range of speech could therefore be avoided if the resonance frequency could be raised.

Considering the above relation (1), a first way of raising the resonance frequency would be to increase the acoustic stiffness Kp of the plug. That is essentially what has been done in the prior-art foam plug. However, this solution results in an undesirably high total attenuation due to the voltage division formed by the two acoustic stiffnesses Kp and Kö according to the relation (2) below, which shows the dependence of the experienced sound pressure Vö on the stiffnesses Kp and Kö:

$$Vö \sim VK\frac{ö}{Kp + Kö} \quad (2)$$

If an attempt is made to raise the resonance frequency Fr by increasing the acoustic stiffness Kp of the plug, the attenuating effect will increase simultaneously with increasing Kp. This phenomenon clearly appears from the corresponding attenuation characteristic in the diagram in FIG. 1, which admittedly shows that the attenuation of the prior-art foam plug has a rather straight characteristic, but is situated at such a high level as 40 dB or more within the range of speech.

A prior art reusable ear plug, such as an ear plug disclosed in EP 0847736, also has a resonance frequency according to the above relation (1). The acoustic stiffness Kp of the reusable plug is lower than that of the foam plug, and has therefore a lower attenuation. However, the resonance frequency of such a reusable plug is within the relevant frequency range, and the attenuation is therefore frequency dependent. One way of raising the resonance frequency would be to increase the acoustic stiffness Kp of the reusable plug, as was done with the prior art foam plug. However, the result would be a stiff ear plug which would be difficult to insert and fit properly in the auditory meatus. A second way of raising the resonance frequency of the reusable ear plug would instead be to reduce the acoustic mass Mp of the plug. However, this solution also entails a number of difficulties.

If, for instance, it is desirable to raise the resonance frequency of the prior-art reusable plug by a factor 10, say from 500 Hz to 5 kHz, the mass of the plug must be reduced by a factor 100, which would cause great manufacturing problems and might not even be possible.

To illustrate how the above-mentioned problems have been solved according to the invention, reference is now first made to FIG. 4, which shows an electric circuit analogy for the prior-art glass down plug which is currently manufactured and sold by the Applicant. Md and Kd indicate the acoustic mass and acoustic stiffness, respectively, of the elastic glass down body 3 which is highly air-flow blocking. Mt indicates the acoustic mass of the foil tip 17 of the sheath 1, i.e. the front tip portion of the sheath 1 in the direction of insertion. Kt indicates the acoustic stiffness of the foil tip 17. Rd indicates the flow resistance of the glass down body 3, said flow resistance being applied in the form of a high-resistive shunt connection over Md and Kd in the electric circuit analogy.

Given the above-mentioned designations, the resonance frequency of this prior-art glass down plug is essentially dependent on acoustic masses and acoustic stiffnesses according to the relation (3) below:

$$Fr \sim \sqrt{\frac{Kd + K\ddot{o} + Kt}{Md + Mt}} \quad (3)$$

The glass down of the elastic body of the prior-art plug has a high flow resistance (high Rd), and therefore the external sound pressure must "accelerate" the acoustic mass Md of the entire down body and overcome the acoustic stiffness Kd.

Figure 5A:
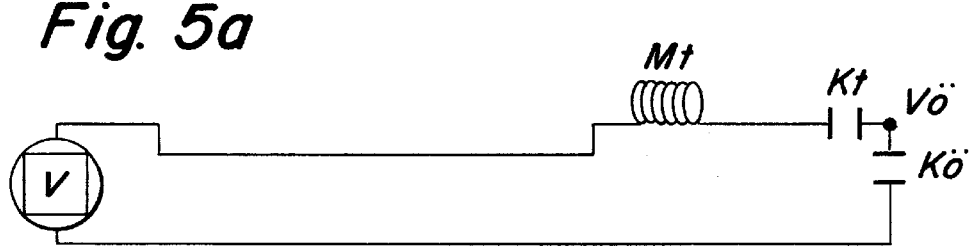
FIGS. 5a and 5b show an electric circuit analogy for an ear plug according to the invention.
Figure 5B:
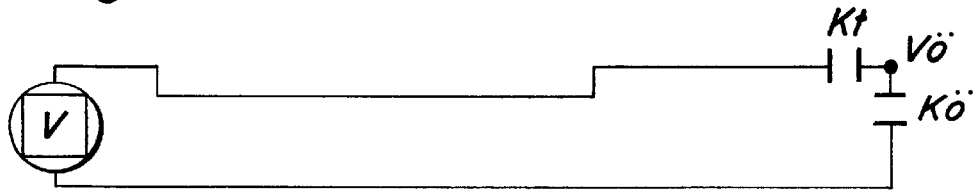

Reference is now made to FIGS. 5*a* and 5*b*, which illustrate the principle of the invention when applied to an ear plug of the kind shown in FIG. 6. In the new construction, the prior-art glass down body 3 which is highly air-flow blocking is replaced by an elastic body 103 which is substantially non-blocking as regards air-flow and which is made, for instance, of a polymer fibre material. This makes the air-flow resistance through the shunt connection Rd in FIG. 4 negligible, resulting in the acoustic mass Md and the acoustic stiffness Kd of the elastic body 103 both being short-circuited. These two components are therefore omitted from FIG. 5*a*. Mt is so small in relation to Kt that Fr will be above the relevant range. This leads to a situation in which the acoustic mass Mt of the rounded, thin and light foil tip 117 has a considerable effect on the resonance frequency.

Furthermore, in FIG. 5*a* the mass Mt of the rounded foil tip 117 is substantially negligible within the frequency range relevant to speech perception. As a result, the voltage division (the distribution of the sound pressure) takes place only over the two acoustic stiffnesses Kt and Kö, as illustrated in FIG. 5*b*. This leads to a substantially frequency-independent voltage division at the point Vö, i.e. substantially frequency-independent attenuation. It is in particular to be noted that the increased stiffness of the foil 117, which is attained owing to its rounded shape, efficiently contributes to the sound attenuation. This may be concluded from the relation (4) below:

$$V\ddot{o} \sim VK \frac{\ddot{o}}{Kt + K\ddot{o}} \quad (4)$$

A high acoustic stiffness Kt of the rounded foil 117 increases the voltage division, i.e. the attenuation.

A particular advantage of the invention is that the sound-attenuating effect of the sound-attenuating ear plug is easy to control by the selection of the thickness of the rounded foil 117. Especially, the attenuation characteristic can be substantially parallel-displaced by such a thickness variation without any other substantial effect on the shape or appearance of the characteristic. This constitutes a great advantage which makes it possible to adapt ear plugs in a simple and cheap manner to various fields of application.

Reference is once more made to the diagram in FIG. 1. The thick, unbroken curve in the middle of the diagram marked "The invention" illustrates the result of measurements made on a manufactured and analysed embodiment of the invention according to FIG. 6. The analysed ear plug was substantially identical with the prior-art glass down plug, but the glass down was completely replaced by polyester fibres or polyester down. As apparent from the diagram, the frequency characteristic of the invention is very close to an ideal, straight characteristic, both below and within the frequency range that is relevant to speech perception. It is not possible to distinguish any crucial break frequency, and the invention has in particular made it possible to raise the high attenuation of the prior-art glass down plug above 1 kHz to a level which is considerably better for speech perception.

The numerical measured values, on which the curves of FIG. 1 are based, are indicated in Table 1 below.

TABLE 1

Attenuation (dB) as a function of frequency

| Test object | Hz | | | | | | | |
|---|---|---|---|---|---|---|---|---|
| | 63 | 125 | 250 | 500 | 1000 | 2000 | 4000 | 8000 |
| Prior-art foam plug | 34 | 34 | 35 | 36 | 36 | 36 | 40 | 43 |
| Prior-art glass down plug | 25 | 25 | 25 | 27 | 27 | 32 | 38 | 38 |
| The invention | 21 | 21 | 22 | 22 | 24 | 25 | 23 | 25 |
| Invention: punctured | 2 | 2 | 4 | 9 | 15 | 18 | 22 | 24 |
| Invention: without tip | 1 | 2 | 1 | 2 | 3 | 4 | 5 | 6 |
| Invention: increased foil thickness | 27 | 26 | 26 | 27 | 29 | 30 | 28 | 28 |
| Ideal (Example) | 17 | 17 | 17 | 17 | 17 | 17 | 17 | 17 |

Table 1 also contains measured values for three modified plugs, where the manufactured ear plug according to the invention has been modified in various ways. Corresponding attenuation characteristics are indicated by dashed curves in the diagram in FIG. 1.

In a first test, the rounded tip 117 of the sheath was cut off. Corresponding measured values clearly show that the attenuation becomes very small for low frequencies and considerably reduced within the speech range.

In a second test, the rounded foil tip 117 was punctured with a needle. Corresponding measured values hardly showed any attenuation for low frequencies, and this test indicates that an airtight foil material should be used in a preferred embodiment of the invention.

In a third test, the thickness of the rounded foil tip was increased. There was substantially no effect on the shape of the attenuation characteristic, but the entire curve was parallel-displaced downwards by about 5 dB.

It can be noted that the rounded foil which according to the invention is responsible for the major part of the sound-attenuating effect of the ear plug cannot be compared to the membranes which are used in some prior-art ear plugs. These prior-art ear plugs provided with a membrane function according to physical principles which are completely different from those of the ear plug according to the invention.

In addition, it should be noted that the object of the elastic body of the ear plug according to the invention is mainly to position the rounded foil in the auditory meatus and to ensure that it fits essentially tightly, directly or indirectly, to the inner wall of the auditory meatus.

The above is a description of a preferred embodiment of the invention in the form of a plug comprising an elastic body, which is made of fibrous material that is substantially non-blocking as regards air-flow and which is surrounded by a sheath of foil material. It is, however, possible to realise the inventive principle also in other types of ear plugs, for instance, foam plugs in which the elastic body is made of a foam material.

The above-described embodiment of FIG. 6 may, for instance, be varied by using foamed polymer material instead of the fibrous filling material. The body 103 still has to be of a type that is substantially non-blocking as regards air-flow. As examples of possible materials, mention can be made of polyurethane and polyvinyl chloride (PVC).

According to a first variant, a prior-art foam plug of the above-described kind is modified by providing the foam body with a through-going central duct in its longitudinal direction and by blocking this duct with at least one rounded, airtight foil according to the invention. This can be realised by arranging the rounded foil inside the duct between the ends of the plug or in direct connection with the inner or front end of the plug.

Another variant consists in modifying a prior-art foam plug by providing the same with an outer foil-like layer, which at that end of the foam plug which is the front end in the direction of insertion has a rounded end portion which is responsible for at least a considerable part of the attenuating effect of the plug.

What is claimed is:

1. A sound-attenuating ear plug, comprising:
    an elongate elastic body adapted to be inserted at least partially into an auditory meatus, said body being essentially non-attenuating as regards sound, and
    a foil held by said body, along a longitudinal axis of said body, said foil having a three-dimensionally rounded concave or convex shape which provides such acoustical properties that the foil is responsible for a major part of a sound-attenuating effect of the ear plug;
    wherein the elastic body is made of a material which has an acoustic resistance which is maximized to $1.2*10^9$ sN/m$^5$.

2. An ear plug as claimed in claim 1, wherein the elastic body is made of a material which is substantially non-blocking as regards air-flow.

3. An ear plug as claimed in claim 2, wherein the foil is essentially dome-shaped and provided on a front tip portion of the elastic body.

4. An ear plug as claimed in claim 3, wherein the ear plug further comprises a sheath which at least partially surrounds the elastic body, the rounded foil, referring to a direction of insertion of the plug into the auditory meatus, thus defining a front tip portion of the sheath.

5. An ear plug as claimed in claim 1, wherein said rounded foil has a frequency independent acoustic compliance which is maximized to $1.7*10-11$ m$^5$/N.

6. An ear plug as claimed in claim 1, wherein said material of the elastic body includes a fibrous material.

7. An ear plug as claimed in claim 6, wherein said fibrous material includes a polymer material.

8. An ear plug as claimed in claim 7, wherein said polymer material is selected from the group consisting of polyester, polypropylene, polyether and polyamide.

9. An ear plug as claimed in claim 6, wherein said fibrous material comprises mutually fixed fibres.

10. An ear plug as claimed in claim 6, wherein said fibrous material comprises mutually non-fixed fibres.

11. An ear plug as claimed in claim 1, wherein said material of the elastic body includes a foamed material.

12. An ear plus as claimed in claim 11, wherein said foamed material is a polymer foamed material.

13. An ear plug as claimed in claim 4, wherein said elastic body is completely surrounded by the sheath.

14. An ear plug as claimed in claim 13, wherein said sheath has a circumferential rigid portion defined by an outwardly directed collar or flange portion, at a rear of the plug.

15. An ear plug as claimed in claim 4, wherein said rounded foil has a greater thickness at least in relation to a remainder of a front portion of the sheath.

16. An ear plug as claimed in claim 4, wherein said sheath is a deep-drawn thermoplastic plastic film or foil.

17. An ear plug as claimed in claim 1, wherein said rounded foil is substantially airtight.

18. An ear plug as claimed in claim 1, wherein said rounded foil has a thickness which does not exceed 0.2 mm.

19. An ear plug as claimed in claim 1, wherein said rounded foil has a thickness which is not less than 0.005 mm.

20. An ear plug as claimed in claim 1, wherein said rounded foil has a thickness in a range of 0.005 mn to 0.2 mm.

21. An ear plug as claimed in claim 1, wherein said rounded foil has a thickness which is adapted to provide a desired attenuating effect of the ear plug.

22. An ear plug as claimed in claim 1, wherein said rounded foil is made of a material selected from the group consisting of polyvinyl chloride (PVC), polyurethane (PUR) and polyethylene (PE).

23. An ear plug as claimed in claim 1, wherein an attenuation of the ear plug is substantially in a range of 10 dB to 30 dB for frequencies up to at least 4 kHz.

24. An ear plug as claimed in claim 1, wherein said rounded foil has a frequency dependent acoustic stiffness which provides for the sound-attenuating effect of said foil, the stiffness being chosen so that, in a frequency range of speech, a substantially frequency-independent sound-attenuating is achieved.

25. An ear plug as claimed in claim 23, wherein an attenuation of the ear plug is substantially in the range of 10 dB to 30 dB for frequencies up to at least 8 kHz.

26. A sound-attenuating ear plug, comprising:
    an elastic body adapted to be inserted into an auditory meatus, said elastic body being made of a material which is substantially non-attenuating as regards sound; and
    a sheath which at least partially surrounds the elastic body, at least a part of said sheath having acoustical properties being responsible for a major part of a sound-attenuating effect of the ear plug;
    wherein the elastic body is made of a material which is substantially non-blocking as regards air-flow and has an acoustic resistance which does not exceed $1.2*10^9$ $sN/m^5$.

27. An ear plug as claimed in claim 26, wherein said at least a part of said sheath has an acoustic compliance which does not exceed $1.7*10^{-11}$ $m^5/N$.

28. A sound-attenuating ear plug comprising:
    a body portion made of a material which has an acoustic resistance no greater than $1.2*10^9$ $sN/m^5$, and an airtight foil which is three-dimensionally rounded in a longitudinal direction of an auditory meatus and arranged so that said rounded foil, during use of the ear plug, directly or indirectly fits substantially tightly to an inner wall of the auditory meatus, wherein the rounded foil is responsible for a major part of a sound-attenuating effect of the ear plug.

29. An ear plug as claimed in claim 28, wherein the body portion comprises an elongate elastic body which is essentially non-attenuating as regards sound and said foil is held in the three-dimensionally rounded shape by the elongate elastic body.

30. A method of manufacturing an ear plug which comprises an elongate body made of elastic material and surrounded by a sheath made of flexible plastic material, the method comprising:
    deep-drawing a thermoplastic plastic film or foil into a sheath; and
    filling the sheath, subsequently or simultaneously, with elastic material, wherein said elastic material includes a material which is substantially non-blocking as regards air-flow and has an acoustic resistance which is maximized to $1.2*10^9$ $sN/m^5$.

31. A method as claimed in claim 30, further comprising forming the sheath with a rounded tip.

32. In a sound-attenuating ear plug comprising an elastic body portion, the improvement comprising:
    the elastic body portion is made of a material which has an acoustic resistance which is maximized to $1.2*10^9$ $sN/m^5$; and
    an airtight foil which is three-dimensionally rounded in a longitudinal direction of an auditory meatus disposed on the body portion;
    wherein the airtight foil is responsible for a major part of a sound-attenuating effect of the ear plug.

33. A method of controlling the sound-attenuating effect of a sound-attenuating ear plug, comprising the steps of:
    providing the ear plug with an elastic body portion and a foil which is three-dimensionally rounded in a longitudinal direction of an auditory meatus;
    choosing a thickness of the rounded foil so as to obtain a desired sound-attenuating effect of the ear plug; and
    choosing a material for the elastic body portion that provides an acoustic resistance which does not exceed $1.2*10^9$ $sN/m^5$.

* * * * *